United States Patent
Benner

(10) Patent No.: US 11,667,942 B1
(45) Date of Patent: Jun. 6, 2023

(54) ASSEMBLY OF LONG DNA MOLECULES BY TRANSLITERATION

(71) Applicant: Steven A Benner, Gainesville, FL (US)

(72) Inventor: Steven A Benner, Gainesville, FL (US)

(*) Notice: Subject to any disclaimer, the term of this patent is extended or adjusted under 35 U.S.C. 154(b) by 40 days.

(21) Appl. No.: 17/121,446

(22) Filed: Dec. 14, 2020

Related U.S. Application Data

(63) Continuation-in-part of application No. 15/997,339, filed on Jun. 4, 2018, now Pat. No. 10,865,431, which is a continuation-in-part of application No. 14/218,405, filed on Mar. 18, 2014, now Pat. No. 9,988,659, which is a continuation-in-part of application No. 12/653,613, filed on Dec. 16, 2009, now Pat. No. 9,334,534.

(51) Int. Cl.
*C12P 19/34* (2006.01)

(52) U.S. Cl.
CPC .................................. *C12P 19/34* (2013.01)

(58) Field of Classification Search
CPC ....................................................... C12P 19/34
See application file for complete search history.

*Primary Examiner* — Jezia Riley

(57) ABSTRACT

Processes described here exploit the utility of mismatching nucleobase analogs to create long segments of natural DNA to be constructed after fragments containing unnatural nucleotides are transliterated in at least two cycles of polymerase-catalyzed copying, or alternatively complete PCR, by guided mismatching.

3 Claims, 5 Drawing Sheets

Figure 1:
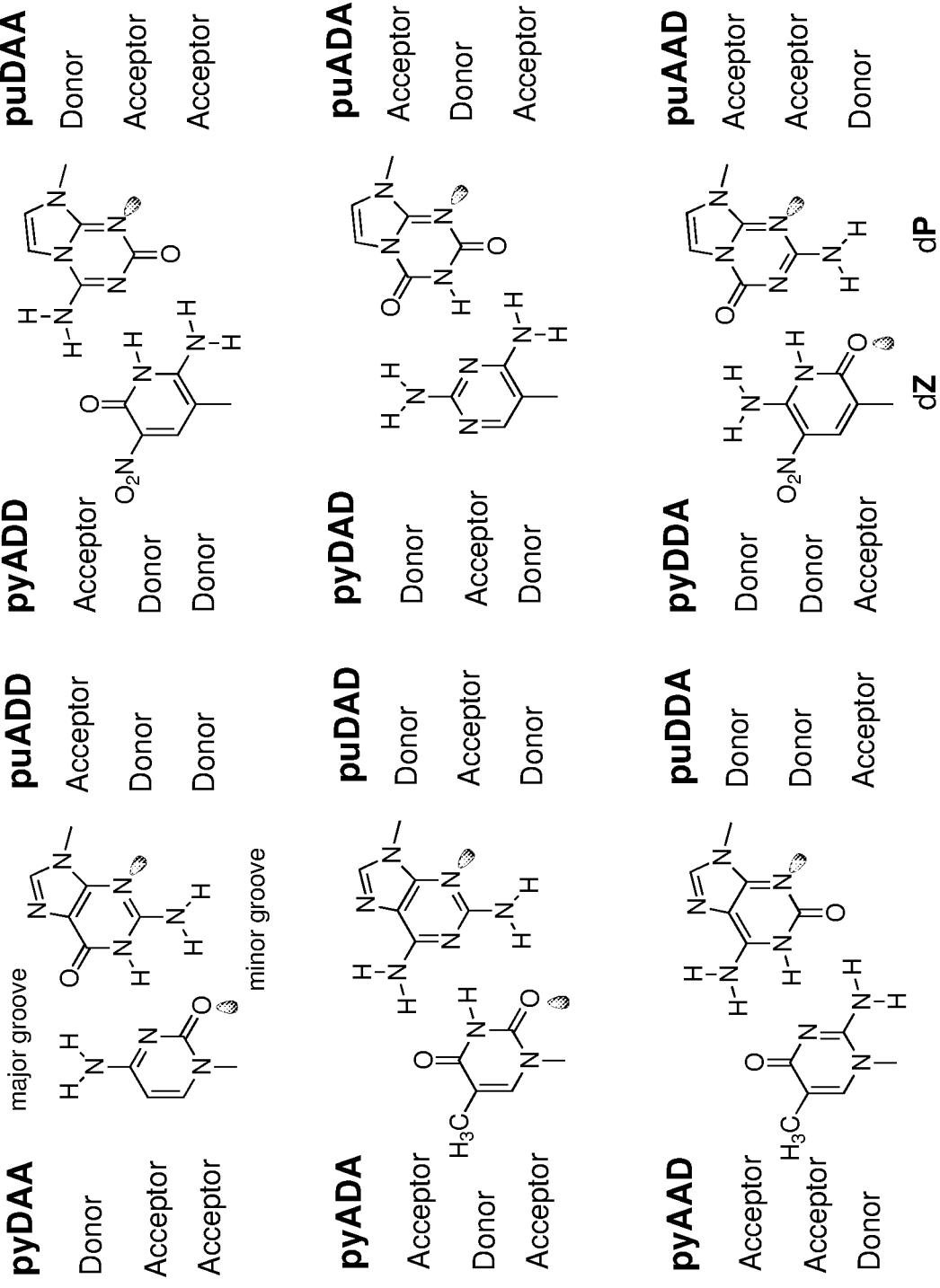

Specification includes a Sequence Listing.

ASSEMBLY OF LONG DNA MOLECULES BY TRANSLITERATION

CROSS REFERENCE TO RELATED APPLICATIONS

This Application is a continuation in part of U.S. patent application Ser. No. 15/997,339, filed 4 Jun. 2018, currently pending, for "Polymerase Incorporation of Non-standard Nucleotides". U.S. patent application Ser. No. 15/997,339 is a continuation in part of U.S. patent application Ser. No. 14/218.405, filed 18 Mar. 2014, now issued as U.S. Pat. No. 9,988,659, for "In Vivo Conversion of Nucleosides in Plasmid DNA". U.S. patent application Ser. No. 14/218,405 is a continuation in part of U.S. patent application Ser. No. 12/653,613, filed 16 Dec. 2009, issued as U.S. Pat. No. 9,334,534, for "Processes replacing standard nucleotides by non-standard nucleotides and non-standard nucleotides by standard nucleotides in DNA". application Ser. No. 12/653,613 claimed benefit of U.S. Provisional Patent Application 61/802,913, filed 18 Mar. 2013. The disclosures of all of these are hereby incorporated by reference in their entirety, including all figures, tables and sequences.

STATEMENT OF RIGHTS TO INVENTIONS MADE UNDER FEDERALLY-SPONSORED RESEARCH

None

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION

(1) Field of the Invention

The field of this invention is nucleic acids and their analogs, and to processes that manipulate DNA, specifically the construction of DNA molecules by the assembly of smaller fragments of DNA by hybridization and, optionally, polymerase extension and/or ligation. Separately, the field of this invention also comprises nucleotide analogs that can form non-standard Watson-Crick nucleobase pairs that have similar geometry as standard Watson-Crick pairs, but are joined by a non-standard hydrogen bonding schemes. More specifically, this invention relates to processes that allow the assembly of multiple small fragments of DNA based on the hybridization of segments containing one or more non-standard nucleotides. More specifically, this invention relates to processes that then replace any non-standard nucleotides by more than one standard nucleotide. Most specifically, this invention relates to processes whereby that replacement occurs in living bacterial cells.

(2) Description of Related Art

Natural oligonucleotides bind to complementary oligonucleotides according to Watson and Crick rules of nucleobase pairing, where adenine (A) (or 2-aminoadenine) pairs with thymine (T) (or uracil, U), and guanine (G) pairs with cytosine (C), with complementary strands anti-parallel to one another. In this disclosure, "DNA" or "nucleic acid" is understood to include, as appropriate, both DNA (where the sugar is 2'-deoxyribose) and RNA (where the sugar is ribose), the 2'-O-alkyl and allyl derivatives, and these nucleic acids and their analogs in non-linear topologies, including dendrimers, comb-structures, and nanostructures, and these nucleic acids and their analogs carrying tags (e.g., fluorescent, functionalized, or binding) to the ends, sugars, or nucleobases, and/or non-nucleotidic material attached to the ends of the strand.

These pairing rules, which are largely context free and which can be applied without undue experimentation even by high school students, allow specific hybridization of an oligonucleotide to a complementary oligonucleotide, making oligonucleotides valuable as probes in the laboratory, in diagnostics, as messages that can direct the synthesis of specific proteins, and in other applications well known in the art. Such base pairing is used, as an example and without limitation, to capture other oligonucleotides to beads, arrays, and other solid supports, in linear and dendrimeric structures, to allow nucleic acids to fold in hairpins, beacons, and catalysts, as supports for functionality, such as fluorescence, fluorescence quenching, binding/capture tags, and catalytic functionality, as part of more complex architectures, including dendrimers and nanostructures, and as scaffolds to guide chemical reactions.

Further, nucleobase pairing is used by enzymes to catalyze synthesis of new oligonucleotides that are complementary to template nucleotides. In this synthesis, building blocks (normally the triphosphates of ribo- or deoxyribonucleosides carrying of A, T, U, C, or G) are directed by a template oligonucleotide to form a complementary oligonucleotide with the complementary sequence. This serves as the basis for technologies for enzymatic synthesis and amplification of specific nucleic acids by enzymes such as DNA and RNA polymerase, in the polymerase chain reaction (PCR), and in a variety of architectures that may involve synthesis, ligation, cleavage, immobilization and release, inter alia, used in technology to detect nucleic acids.

The Watson-Crick pairing rules can be understood chemically as a consequence of the arrangement of hydrogen bonding groups on the heterocyclic nucleobases of the oligonucleotide, groups that can either be hydrogen bond donors or acceptors. In the standard Watson-Crick geometry, a large purine nucleobase pairs with a small pyrimidine nucleobase. Thus, the AT nucleobase pair is the same size as a GC pair. In this disclosure, to be "complementary in the Watson-Crick sense" means to have the Watson-Crick geometry, a full pairing (not wobble pairing) of a large purine and a small pyrimidine held together by three hydrogen bonds, or (if context demands) two hydrogen bonds, where in pairing is said to be "against" the nucleotide in the complementary strand, in an antiparallel orientation, to which it is matched.

The specificity of recognition between large and small nucleobases is determined by hydrogen bonding between the nucleobases. In standard nucleobases, hydrogen bond donors are heteroatoms (nitrogen or oxygen in the natural nucleobases) bearing a hydrogen, while hydrogen bond acceptors are heteroatoms (nitrogen or oxygen in the natural nucleobases) with a lone pair of electrons. In the Watson-Crick nucleobase pairing geometry, a six membered ring (in standard nucleobases, a pyrimidine) pairs with a ring system composed of a fused five-six ring system (in standard nucleobases, a purine), with a middle hydrogen bond linking two ring atoms, and hydrogen bonds on either side joining functional groups appended to each of the rings, with donor groups paired with acceptor groups. The AT nucleobase pair uses this hydrogen bonding pattern only partly; it is completely used in the diaminoA:T base pair.

In 1990, the instant Inventor filed the first patent application (which later issued as U.S. Pat. No. 5,432,272) disclosing compositions of matter that expanded the number of nucleobases that could pair by such simple rules. He proposed eight additional nucleobases that form four additional pairs by changing the pattern of hydrogen bond donor and acceptor groups presented by a nucleobase to the nucleobase on a complementary oligonucleotide analog [U.S. Pat. Nos. 5,432,272, 5,965,364, 6,001,983, 6,037,120, 6,140,496, 6,627,456, 6,617,106]. These disclosures showed that the geometry of the Watson-Crick nucleobase pair could accommodate as many as 12 nucleobases forming 6 mutually exclusive pairs. Of these, four nucleobases forming two pairs are "standard", while eight nucleobases forming four pairs were termed "non-standard". Adding the non-standard nucleobases to the standard nucleobases yielded an Artificially Expanded Genetic Information System (AEGIS). It was also noted that these nucleobases analogs might be functionalized to enable a single biopolymer capable of both genetics and catalysis.

Expanded genetic alphabets have been explored [Swi89] [Pic90][Pic91][Voe93] [von95] [Voe96a][Voe96b][Kod97] [Jur98][Lut99][Jur99][Jur00]; their contents are incorporated by reference.

To systematize the nomenclature for the hydrogen bonding patterns, the hydrogen bonding pattern implemented on a small component of a nucleobase pair are designated by the prefix "py". Following this prefix is the order, from the major groove to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Again following the prefix, the hydrogen bond donor and acceptor groups are designated, from the major to the minor grooves, using "A" and "D". Thus, the standard nucleobases adenine and guanine implement the standard hydrogen bonding patterns puDA-and puADD respectively.

A teaching of this disclosure is that hydrogen-bonding patterns designated using this systematic nomenclature are distinct in concept from the organic molecules that are used to implement the hydrogen-bonding patterns. Thus, guanosine is a nucleoside that implements the puADD hydrogen-bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups. Which organic molecule is chosen to implement a specific hydrogen-bonding pattern determines, in large part, the utility of the non-standard hydrogen-bonding pattern, in various applications to which it might be applied.

The additional nucleobase pairs, because of their desirable pairing properties, chemical stability, and other features known to those skilled in the art, have been useful for a variety of purposes. For example, the nucleobase pair between 2-amino-5-methyl-1-(1'-beta-D-2'-deoxyribofuranosyl)-4(1H)-pyrimidine, also known as 2'-deoxyisocytidine, disoC, or sometimes (less correctly) isoC and implementing the pyAAD hydrogen bonding pattern, and 6-amino-1, 9-dihydro-9-(1'-beta-D-T-deoxyribofuranosyl)-3H-purin-2-one, also known as 2'-deoxyisoguanosine, disoG, or sometimes (less correctly) isoG, and implementing the puDDA hydrogen bonding pattern, is incorporated into the branched DNA diagnostics tools marketed today by Bayer and its successor, Siemens. Here, the non-standard nucleobase pair supports orthogonal molecular recognition in aqueous solution, similar to nucleic acids but with a coding system that is orthogonal to the system in DNA and RNA, Thus, it allows the assembly of the branched dendrimer in the assay free from inhibition by adventitious nucleic acid, and prevents adventitious nucleic acid from capturing signaling elements form the nanostructure in the absence of the target analyte nucleic acid, creating noise. Further, adding extra letters to the genetic alphabet speeds hybridization, presumably because it decreases the number of close mismatches where DNA dwells before finding its fully matched partner. The branched DNA assay has FDA-approval and is widely used to provide personalized patient care in the clinic.

One advantage of incorporating non-standard nucleotides into human diagnostic assays is that binding between oligonucleotides containing these can occur without interference from natural DNA, which is often present in abundance in samples taken from human tissues. Such binding is often used to concentrate samples from complex mixtures, on arrays or at the bottoms of plastic wells. Natural DNA, built from A, T, G, and C, will interfere with A:T and G:C interactions. This leads to large amounts of noise in DNA arrays, for example. Accordingly, in the branched DNA assays, non-standard nucleotides are incorporated by chemical synthesis into the portion of tags that are used to move the analyte to a spot where it can be detected and to assemble signaling dendrimers.

Pairing between non-standard nucleotides cannot be used to directly bind natural analytes, as these analytes are themselves built from A, T, G, and C. Accordingly, when non-standard nucleotides are used to achieve orthogonality in clinical diagnostic assays [Elb04a][Elb04b], they are general appended as tags to primary probes, which are built from A, T. G, and C. The primary probes are the ones that contact the analyte targeted by the diagnostic assay. This limits considerably the use of non-standard components to achieve orthogonality and high signal-to-noise ratios in biological systems. A process that creates replicates or complements of oligonucleotides that replace in a controlled fashion standard nucleotides by non-standard nucleotides would therefore have utility. If this is sequence specific, the pairing of the resulting replicate or complement through non-standard base pairs could, in an appropriate architecture, offer an element of selectivity for the analyte in addition to those selectivity elements based on other regions of the analyte (for example, the regions that bind PCR amplification primers).

Conversely, oligonucleotides containing non-standard nucleotides cannot today be introduced into standard cloning systems. No strain used for cloning, including E. coli strains, is known to have the cellular machinery for making the triphosphates of non-standard nucleosides and using them to replicate DNA containing non-standard nucleotides. A process that creates replicates or complements of oligonucleotides that replace in a controlled fashion non-standard nucleotides by standard nucleotides (a vice versa process) would therefore have utility. Further, such a process would most useful if it is a process pair, where the product from one process replaces the non-standard nucleotide by one standard nucleotide, and another replaces the non-standard nucleotide by a different standard nucleotide. This makes it possible to compare the sequences of the two resulting replicates or complements to ascertain where in the oligonucleotide sequence the original non-standard nucleotide(s) was (were) found.

Mismatching is known between non-standard and standard pairs such that a standard nucleotide is incorporated opposite a nonstandard nucleotide in the template. For example, Sepiol et al. [Sep76] recognized that isoG, which presents a hydrogen bond donor-donor-acceptor pattern complementary to the acceptor-acceptor-donor pattern of isoC, exists in water to about 10% as an enol tautomeric form, which can present a hydrogen bond donor-acceptor-donor hydrogen bonding pattern complementary to T (acceptor-donor-acceptor). Work in the 1990's showed that polymerases of various types would incorporate T (or U) opposite isoG in a template, presumably by pairing between T (or U) and the minor tautomeric form of isoG [Swi93]. This caused the loss of the isoG:isoC pair in (for example) PCR reactions [Joh04], a loss that was considered throughout the art to be disadvantageous, as it appeared to deprive the product from the possibility of the PCR product of having the orthogonal isoC:isoG pair.

Struggling to suppress this mispairing between T and the minor tautomeric form of isoG, the instant Inventor and Michael Sismour exploited the discovery that the minor tautomer of isoG does not pair well with 2-thio, and replaced T with 2-thioT in a polymerase incubation [Sis05]. Therefore, products derived from a six letter PCR incorporating A, G, C, 2-thioT, isoG and isoC was able to retain the isoC and isoG non-standard components after many more cycles than a six letter PCR where standard T was used instead of 2-thioT. Thus, the products were able to retain the ability to be orthogonally bound by isoG:isoC pairing after many more cycles of PCR. Further attempting to avoid mispairing and isoG:T (or U) mismatching, 7-deazaisoG was developed [Mar04].

These examples from the prior art show the extent to which those in the art view as undesirable the mismatching between standard nucleotides and non-standard nucleotides, and thereby teach away from the instant invention, which is based on an inventive step that recognizes the utility of mismatching.

BRIEF SUMMARY OF THE INVENTION

This invention is based on the discovered utility of mismatching AEGIS Z opposite standard G, and mismatching of AEGIS B opposite the standard T (as defined in FIG. 1). Under specific conditions disclosed herein, this mismatching can allow a segment of DNA duplex that includes S:B and Z:P pairs, upon PCR amplification, to be transliterated into standard nucleotides with substantial control over the replacement, with Z:P pairs substantially being replaced by C:G, and S:B pairs being substantially replaced by T:A. Here, "substantially" means>95%.

BRIEF DESCRIPTION OF THE SEVERAL VIEWS OF THE DRAWING(S)

FIG. 1. One example of an "artificially expanded genetic information system" (AEGIS). Nucleobase pairs in this system have a Watson-Crick geometry, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. The heterocycles shown are the currently preferred implementations of the indicated hydrogen bonding patterns; others are conceivable. Electron density presented to the minor groove is shown by the shaded lobes. Note that some non-standard pyrimidines do not present this density. The nucleotides implementing the pyDDA:puAAD hydrogen bonding pattern, the topic of this paper, are at the bottom right.

Figure 2:
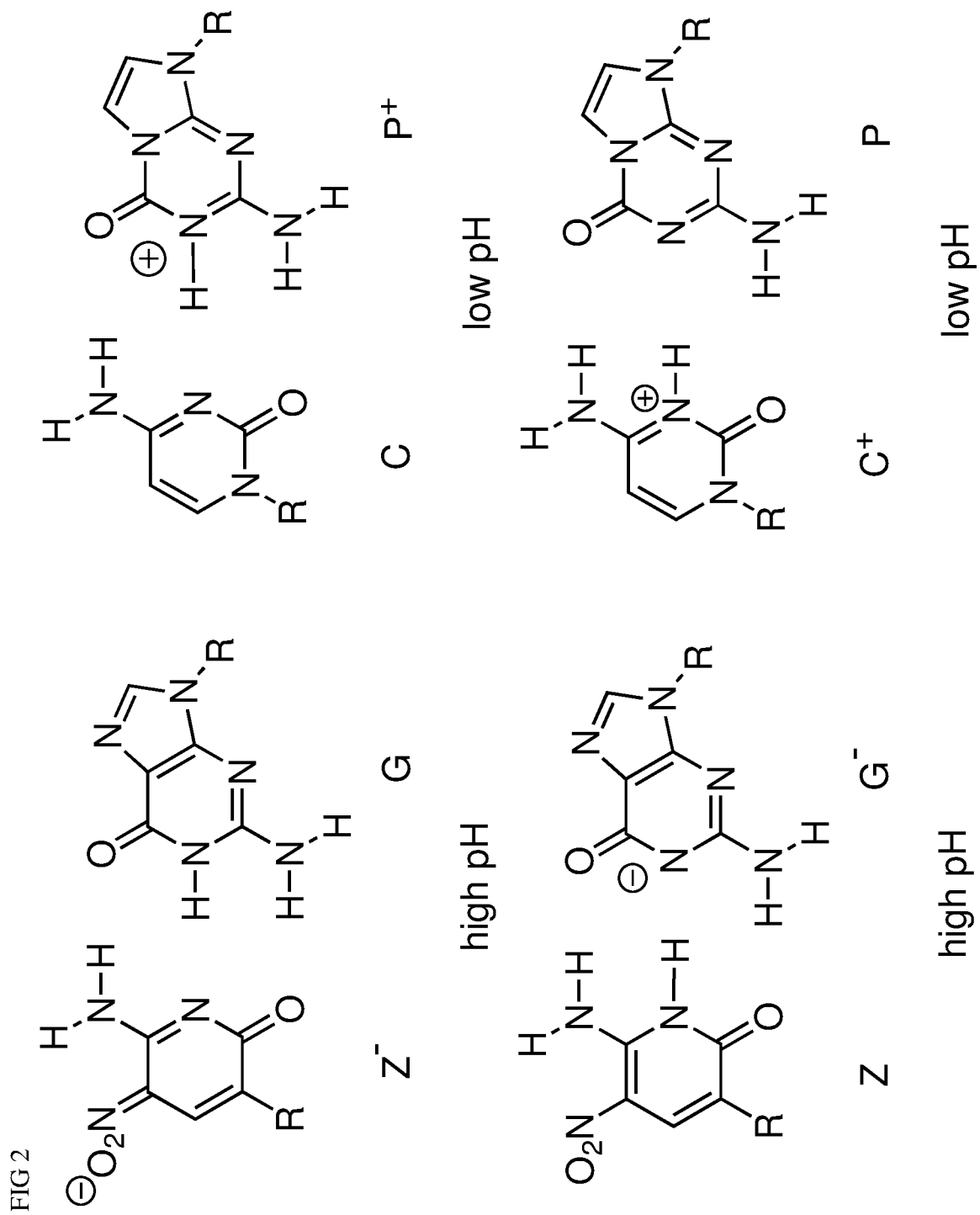

FIG. 2. Mismatches between deprotonated AEGIS Z and standard G, as well as protonated standard C and AEGIS P.

Figure 3:
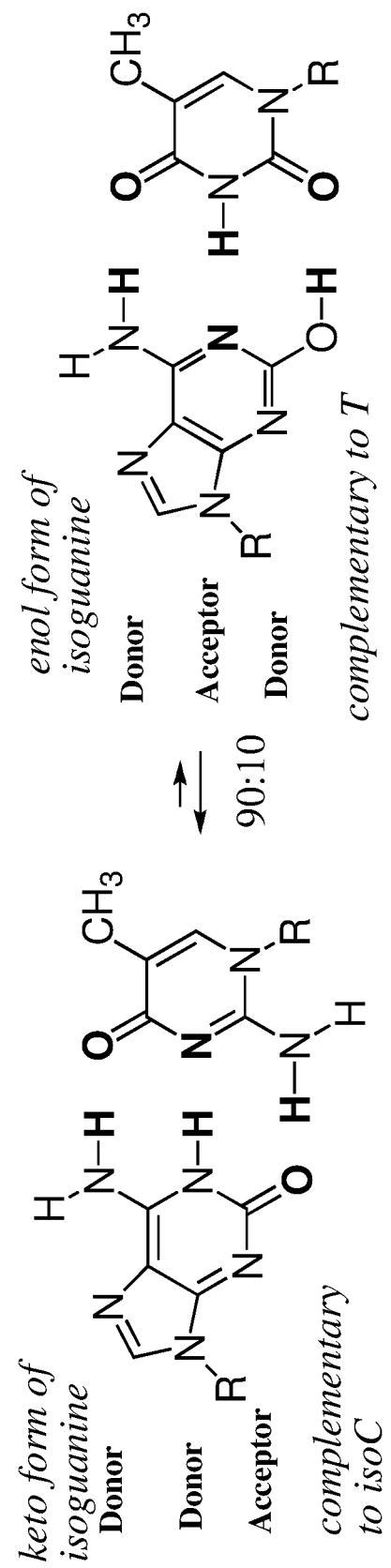

FIG. 3. Mismatches between tautomerized AEGIS B and standard T.

Figure 4:
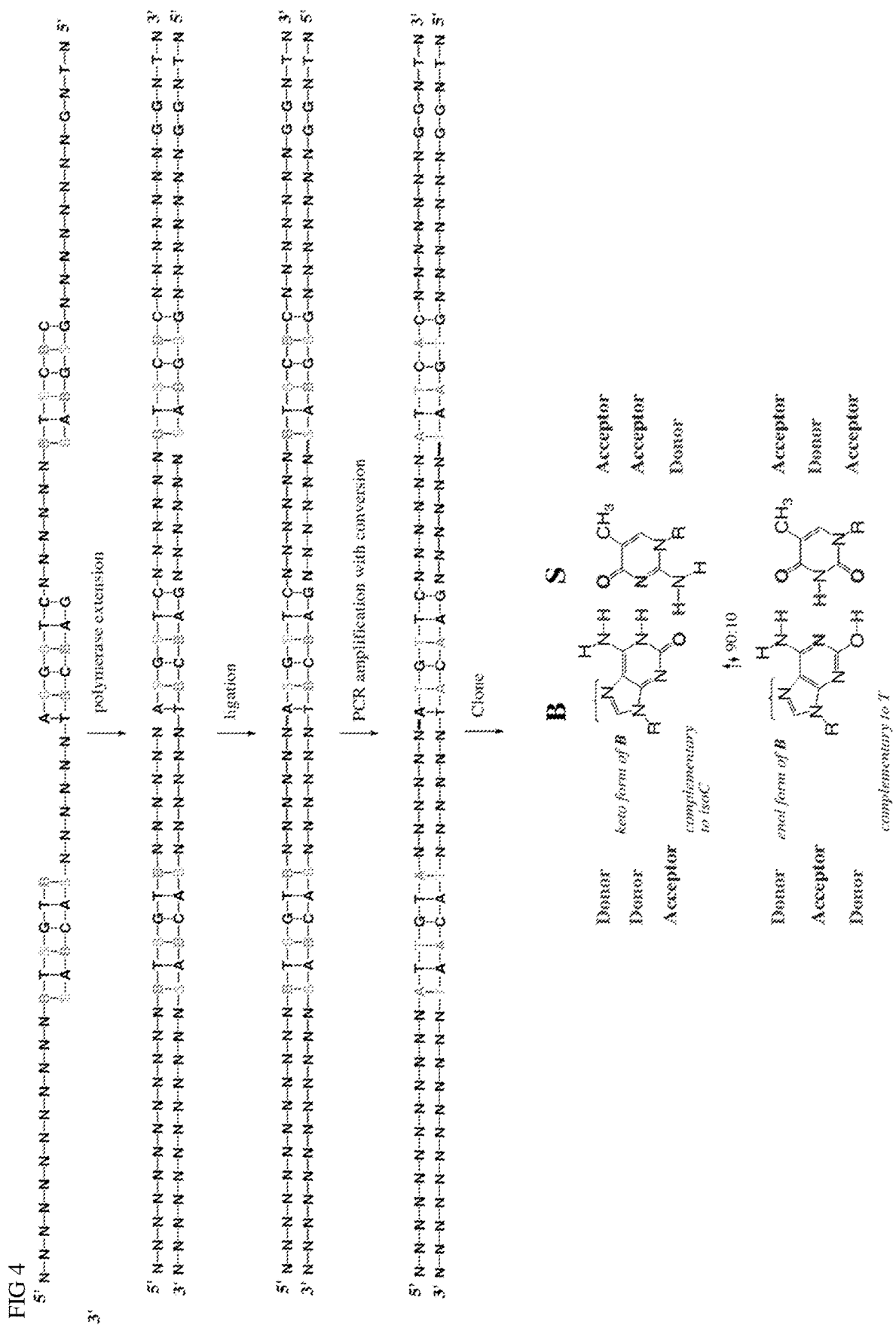

FIG. 4. Schematic of a procedure to create DNA constructs that exploits (a) an increased number of independently pairing nucleotides in synthetic DNA, (b) the orthogonality of pairing between these to allow the synthetic biologists more control over the assembly of synthetic DNA fragments, and (c) polymerases that make the matches under the indicated conditions to delivers a final, an entirely transliterated construct. This is illustrated with S and B, with B:T mismatches producing transliteration.; an analogous process described in the examples exploits Z and P, with Z:G mismatches producing transliteration.

Figure 5:
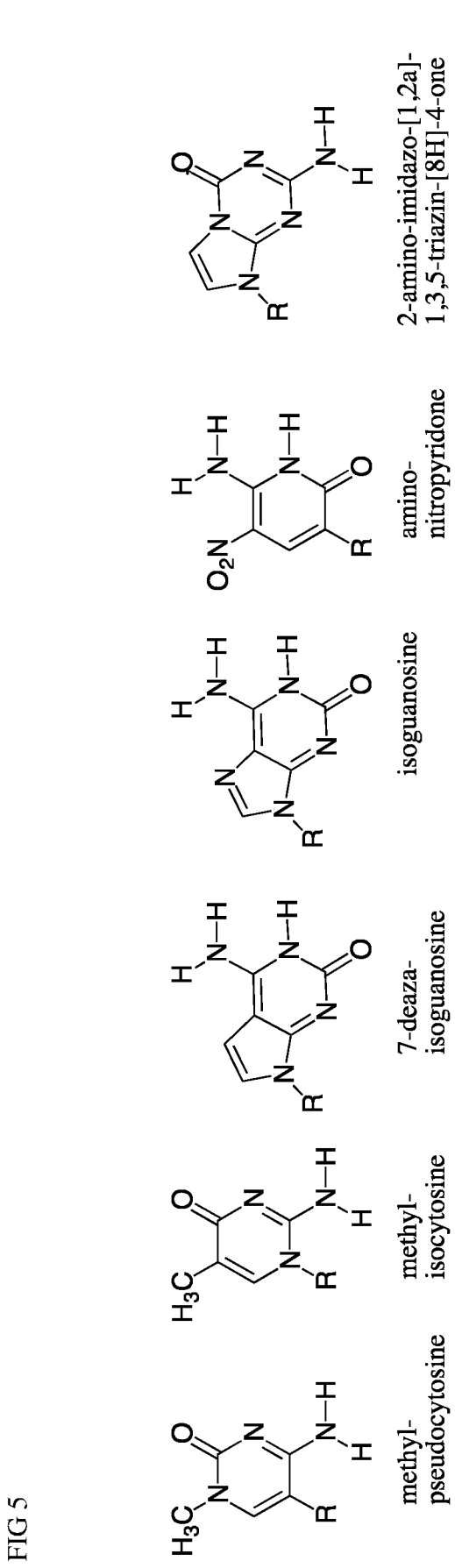

FIG. 5. Presently preferred implementations of the pyrimidine acceptor-acceptor donor hydrogen bonding pattern (methyl-pseudocytosine and methyl-isocytosine), the purine donor-donor-acceptor hydrogen bonding pattern (7-deaza-isoguanosine and isoguanosine), the pyrimidine donor-donor-acceptor hydrogen bonding pattern (amino-nitropyridone), and the purine acceptor-acceptor-donor hydrogen bonding pattern (2-amino-imidazo-[1,2a]-1,3,5-triazin-[8H]-4-one).

DETAILED DESCRIPTION OF THE INVENTION

The presently preferred method for practicing the instant invention assembles four or more DNA oligonucleotide fragments following the schematic shown in FIG. 4. Here, each internal fragment (that is, a fragment that will not end up at the end of the construct) has three regions:
(i) A region (a 5'-hybridizing region) at its 5'-end that can hybridize to the 5'-end of another fragment.
(ii) A region (a 3'-hybridizing region) at its 3'-end that can hybridize to the 3'-end of another fragment.
(iii) Optionally, a third region between the 5'-hybridizing region and the 3'-hybridizing region that does not hybridize to any other region.

The end fragments (should the target construct be linear, rather than circular) lack one or the other of these hybridizing regions. Thus, the 5'-end of the linear construct will have a 3'-hybridizing region, but not a 5'-hybridizing region. Alternatively, the ends might be made in blunt end duplex form. The details of the end assembly are not critical to the inventive portions of this invention.

Annealing of the fragments yields a concatamer., where the 3'-hybridizing region of the first (5'-end) top strand (making reference to FIG. 4) hybridizes to the 3'-hybridizing region of the last (3'-end) bottom strand. Then, the 5'-hybridizing region of the last bottom strand hybridizes to the 5'-hybridizing region of the second top strand. Further bottom and top strands then can anneal to form a complete concatamer.

The schematic in FIG. 4 shows third regions (the 6 consecutive Ns) that are not hybridized in the concatamer. If the 5'-hybridizing regions and 3'-hybridizing regions are long enough, these third regions need not exist. The concatamer can therefore be instantly assembled by ligation using an enzyme ligase. If unhybridized third regions exists in the concatamer, these can be filled in by a DNA polymerase that does not do strand displacement. The filled in product can then have its nicks ligated, to give the full length product, the desired target construct.

As described, this assembly is neither novel nor inventive. The inventive component arises from the use of non-standard nucleotides to assist the assembly. In the schematic shown in FIG. 4, the non-standard nucleotides S and B are placed in the 3'- and 5'-hybridizing regions. The specific sequences of these regions are designed to ensure that the hybridization using Watson-Crick pairing rules expanded to include non-standard nucleobase pairs. This increases the information density in the fragments overall, ensuring the correct assembly of the fragments. Further, the non-standard nucleotides are, by design, placed at sites where, after conversion, the standard nucleotide desired in the construct is created.

The S:B pair is most presently preferred; the Z:P pair is also presently preferred. Other pairs are possible according to conversion rules known in the art.

Thus, the inventive step involves the used of extra non-standard nucleotides to increase the information density of the fragments as they are assembled via annealing to give a concatamer. Also inventive is the conversion of non-standard nucleotides, after their value in directed assembly is used, to standard nucleotides. This is done by the final process, which is the copying of the ligated construct by a DNA polymerase that performs the conversion. This can be done in vivo, in E. coli, where the design ensures that the rules of conversion yield, after conversion, the sequence that is desired in the final target construct. These are shown in Example 1.

Conversion can be done in vitro, using conditions that provide rule-based conversions. Example 2 shows this conversion with S:B as the non-standard pair, with the conversion replacing S:B pairs in the initial ligated construct by T:A pairs in the final construct.

EXAMPLES

PatentAEGISconvertExamplesProvenance

To demonstrate the steps of the instant invention, a pair of nucleoside analogs that contain hereocycles that implement the pyDDA hydrogen bonding pattern on an aminopyridone skeleton, 6-amino-3-(2'-deoxy)-D-ribofuranosyl)-5-nitro-1H-pyridin-2-one (dZ), and that implement the puAAD hydrogen bonding pattern in 2-amino-1,9-dihydro-5-aza-3, 7-dideaza -9-(1'-beta-D-2'-deoxyribofuranosyl)-1H-purin-6-one (dP) were examined. These two heterocycles are complementary in the Watson-Crick sense, in that the large dP is size complementary to the small dZ, and the hydrogen bond donating and accepting groups of dP complement those of dZ when the two are paired in a standard Watson-Crick double helix.

Example 1.

Purpose: Incorporating dZ into oligonucleotides opposite dG via primer extension using THERMINATOR™ DNA polymerase.

Summary of the results: The dZ containing oligo can be efficiently generated through primer extension using standard template and THERMINATOR™ DNA polymerase. These data are shown in FIG. 7 and FIG. 8 of U.S. Pat. No. 9,334,534.

Oligonucleotides used in this example:

Oligonucleotides for glyceraldehyde-3-phosphate dehydrogenase (GAP) Lua3-Std24-Biot:

3'-CTA ACA TTC TAA ACT ATT TCA CAT-Biot-5' SEQ ID NO 1

3'-CTA ACA TTC TAA ACT ATT TCA CAT-GGACTGGACGGCAGATCTTTT-Biot-5' SEQ ID NO 2

GAP-prim-21-Biot: 3'-ZTA AZA TTZ TAA AZT ATT TZA ZAT-GGACTGGACGGCAGATCTTTT-Biot-5' SEQ ID NO 3

GAP-F-Std45: 5'-GAT TGT AAG ATT TGA TAA AGT GTA CCTGACCTGCCGTCTAGAAAA-3' SEQ ID NO 4

GAP-prim-21-Biot: 3'-CTA AZA TTZ TAA AZT ATT TZA ZAT-GGACTGGACGGCAGATCTTTT-Biot-5' SEQ ID NO 5

GAP-F-45-5P: 5'-GAT TPT AAP ATT TPA TAA APT PTA CCTGACCTGCCGTCTAGAAAA -3' SEQ ID NO 6

Oligonucleotides for topoisomerase (TOP)

Lua10-Std24-Biot: 3'-ACA TCT AAA CAT ACA TAC ATA CTA-Biot-5' SEQ ID NO 7 3'-ACA TCT AAA CAT ACA TAC ATA CTA-CTGTCGGGGCCTACTCTTG-Biot-5' SEQ ID NO 8

TOP-prim-19-Biot: 3'-AZA TZT AAA ZAT AZA TAZ ATA ZTA-CTGTCGGGGCCTACTCTTG-Biot-5' SEQ ID NO 9

Top-F-Std43: 5'-TGT AGA TTT GTA TGT ATG TAT GAT GACAGCCCCGGATGAGAAC-3' SEQ ID NO 10

TOP-prim-19-Biot: 3'-ACA TZT AAA ZAT AZA TAZ ATA ZTA-CTGTCGGGGCCTACTCTTG-Biot-5' SEQ ID NO 11

Top-F-43-5P: 5'-TGT APA TTT PTA TPT ATP TAT PAT GACAGCCCCGGATGAGAAC-3' SEQ ID NO 12

Oligonucleotides for human epidermal growth factor (HBE)

Lua14-Std24-Biot: 3'-TTT CAT ATC ATT CTA CAT ATC ATC-Biot-5' SEQ ID NO 13 3'-TTT CAT ATC ATT CTA CAT ATC ATC-CGGGGTCAACGGCAGATCCT-Biot-5' SEQ ID NO 14

HBE-prim-20-Biot: 3'-TTT ZAT ATZ ATT ZTA ZAT ATZ AT-CGGGGTCAACGGCAGATCCT-Biot-5' SEQ ID NO15

HBE-F-Std43: 5'-AAA GTA TAG TAA GAT GTA TAG TA GCCCCAGTTGCCGTCTAGGA-3' SEQ ID NO 16

HBE-prim-20-Biot: 3'-TTT ZAT ATZ ATT ZTA ZAT ATZ AT-CGGGGTCAACGGCAGATCCT-Biot-5' SEQ ID NO 15

HBE-F-43-5P: 5'-AAA PTA TAP TAA PAT PTA TAP TA GCCCCAGTTGCCGTCTAGGA -3' SEQ ID NO 17

Oligonucleotides for the Myc gene (MYC)

Lua19-Std24-Biot: 3'-CAT AAA CTC ATT CAT TAA CTA ACT-Biot-5' SEQ ID NO 18 3'-CAT AAA CTC ATT CAT TAA CTA ACT-AGGAGGAATACGGAGATAGTA-Biot-5' SEQ ID NO19

MYC-prim-21-Biot: 3'-ZAT AAA ZTZ ATT ZAT TAA ZTA AZT-AGGAGGAATACGGAGATAGTA-Biot-5' SEQ ID NO 20

MYC-F-Std45: 5'-GTA TTT GAG TAA GTA ATT GAT TGA TCCTCCTTATGCCTCTATCAT-3' SEQ ID NO21

MYC-prim-21-Biot: 3'-CAT AAA ZTZ ATT ZAT TAA ZTA AZT-AGGAGGAATACGGAGATAGTA-Biot-5' SEQ ID NO22

MYC-F-45-5P: 5'- GTA TTT PAP TAA PTA ATT PAT TPA TCCTCCTTATGCCTCTATCAT -3' SEQ ID NO 23

Protocol for the primer extension:

|  | 1 | 2 | 3 | 4 | 5 |
|---|---|---|---|---|---|
| γ-$^{32}$P-Primer (1 μM) | 0.1 μL | 0.1 μL | 0.1 μL | 0.1 μL | 0.1 μL |
| Biotin-Primer (1 μM) | 2 μL | 2 μL | 2 μL | 2 μL | 2 μL |
| Template (2 μM) | 1.5 μL Std-Temp | 1.5 μL Std-Temp | 1.5 μL Std-Temp | 1.5 μL dP-Temp | 1.5 μL dP-Temp |
| 10× Thermopol Buffer (pH 9.0) | 1 μL | 1 μL | 1 μL | 1 μL | 1 μL |
| dNTP (1 mM) | 1 μL dA, T, G/TP | 1 μL dNTP | 1 μL dA, T, G, Z/TP | 1 μL dNTP | 1 μL dNTP + dZTP |
| DNA polymerase (1 U/μL) | 1 μL Therminator | 1 μL Therminator | 1 μL Therminator | 1 μL Taq | 1 μL Taq |
| H$_2$O (final volume of 10 μl) | 3.5 μL | 3.5 μL | 3.5 μL | 3.5 μL | 3.5 μL |

Note:
1 (negative control): Therminator, dATP + dTTP + dGTP; 2 (positive control): Therminator, dATP + dTTP + dGTP + dCTP; 3 (experiment): Therminator, dATP + dTTP + dGTP + dZTP; 4 (negative control): Taq, dNTP; 5 (experiment): Taq, dNTP + dZTP.

Primer extension with $^{32}$P-labeled primer:

5'-$^{32}$P-Labeled primer (0.1 pmole plus cold primer (biotin-primer) 2 pmole, final assay concentration 210 nM) was annealed to either standard template or dP containing template (3 pmole, final assay concentration 300 nM) in thermpol reaction buffer by heating (5 min 95° C.) and then slow cooling (0.5 h) to room temperature. dNTP and DNA polymerase were added at room temperature, followed by incubating at 72° C. for 1 min or 5 min, and then, quenched by dilution into PAGE loading/quench buffer (8 μL, 10 mM EDTA in formamide). Samples were resolved by electrophoresis using a 16% PAGE (7 M urea). The gel was analyzed using MolecularImager software.

Primer extension without $^{32}$P labeled primer:

Biotin-labeled primer (2 pmole, final assay concentration 200 nM) was annealed to either standard template or dP containing template (3 pmole, final assay concentration 300 nM) in thermpol reaction buffer by heating (5 min 95° C.) and then slow cooling (0.5 h) to room temperature. The biotin-labeled primer was extended under three different conditions: 2 (positive control): Therminator, dNTP; 3 (experiment): Therminator, dATP+dTTP+dGTP+dZTP; 5 (experiment): Taq, dNTP+dZTP. dNTP and DNA polymerase were added at room temperature, followed by incubating at 72° C. for 5 min. The reaction was quenched with 2 μL of 20 mM EDTA, and diluted with 190 μL of ddH$_2$O to give the fully extended full-length dZ containing or control oligonucleotide (final concentration 10 fmoles/μL). 1 (negative control): Therminator, dATP+dTTP+dGTP; 2 (positive control): Therminator, dATP+dTTP+dGTP+dCTP; 3 (experiment): Therminator, dATP+dTTP+dGTP+dZTP; 4 (negative control): Taq, dNTP; 5 (experiment): Taq, dNTP+dZTP.

Example 2. Capture of the Converted Oligonucleotides on Luminex Beads

Purpose: The method of the instant invention is especially useful if the products of the prime extension process that incorporate a non-standard nucleotide (here, dZ, implementing the pyDDA hydrogen bonding pattern) can be captured on a capture tag that is complementary, and contains dP in the oligonucleotide. This capture is "orthogonal", in the sense that no natural oligonucleotide contains either dP or dZ. Therefore, no natural nucleotide can interfere with the capture. In this experiment, three different products are captured on three different Luminex beads, to which dP-containing oligonucleotides have been attached by preparing them with a 5'-amino group using solid phase synthesis, and coupling to beads carrying-COOH groups with water-soluble carbodiimide, following standard procedures. These are visualized by their capture of a biotinylated oligonucleotide, which captures a fluorescent phycoerythrin fluor, following standard procedures described by the Luminex users manual.

Oligonucleotides used:

B-type beads mixture: coupling standard oligo to MicroPlex COOH Beads:

GAP-F-Lu3-NH2: 5'-NH$_2$-C$_{12}$-GAT TGT AAG ATT TGA TAA AGT GTA -3' (B-Mix-GAP) SEQ ID NO 24

Top-F-Lu10-NH2: 5'-NH$_2$-C$_{12}$-TGT AGA TTT GTA TGT ATG TAT GAT -3' (B-Mix-TOP) SEQ ID NO 25

HBE-F-Lu14-NH2: 5'-NH$_2$-C$_{12}$-AAA GTA TAG TAA GAT GTA TAG TAG -3' (B-Mix-HBE) SEQ ID NO 26

MYC-F-Lu19-NH2: 5'-NH$_2$-C$_{12}$-GTA TTT GAG TAA GTA ATT GAT TGA -3' (B-Mix-MYC) SEQ ID NO 27

C-type beads mixture: coupling dP containing oligo to MicroPlex COOH Beads:

GAP-F-Lu3-NH2-5P: 5'-NH$_2$-C$_{12}$-GAT TPT AAP ATT TPA TAA APT PTA -3' (C-Mix-GAP) SEQ ID NO 28

Top-F-Lu10-NH2-5P: 5'-NH$_2$-C$_{12}$-TGT APA TTT PTA TPT ATP TAT PAT -3' (C-Mix-TOP) SEQ ID NO 29

HBE-F-Lu14-NH2-5P: 5'-NH$_2$-C$_{12}$-AAA PTA TAP TAA PAT PTA TAP TAG -3' (C-Mix-HBE) SEQ ID NO 30

MYC-F-Lu19-NH2-5P: 5'-NH$_2$-C$_{12}$-GTA TTT PAP TAA PTA ATT PAT TPA -3' (C-Mix-MYC) SEQ ID NO 31

Complementary biotin labeled oligonucleotides:

GAP: 2. 3'-CTA ACA TTC TAA ACT ATT TCA CAT-GGACTGGACGGCAGATCTTTT-Biot-5' SEQ ID NO 2

GAP-F-Std45: 5'-GAT TGT AAG ATT TGA TAA AGT GTA CCTGACCTGCCGTCTAGAAAA-3' SEQ ID NO 4

3. GAP-prim-21-Biot: 3'-ZTA AZA TTZ TAA AZT ATT TZA ZAT-GGACTGGACGGCAGATCTTTT-Biot-5' SEQ ID NO 3

GAP-F-Std45: 5'-GAT TGT AAG ATT TGA TAA AGT GTA CCTGACCTGCCGTCTAGAAAA-3' SEQ ID NO 4

TOP: 2.3'-ACA TCT AAA CAT ACA TAC ATA CTA-CTGTCGGGGCCTACTCTTG-Biot-5' SEQ ID NO 8

Top-F-Std43: 5'-TGT AGA TTT GTA TGT ATG TAT GAT GACAGCCCCGGATGAGAAC-3' SEQ ID NO 10

3.TOP-prim-19-Biot: 3'-AZA TZT AAA ZAT AZA TAZ ATA ZTA-CTGTCGGGGCCTACTCTTG-Biot-5' SEQ ID NO 9

Top-F-Std43: 5'-TGT AGA TTT GTA TGT ATG TAT GAT GACAGCCCCGGATGAGAAC-3' SEQ ID NO 10

HBE: 2. 3'-TTT CAT ATC ATT CTA CAT ATC ATC-CGGGGTCAACGGCAGATCCT-Biot-5' SEQ ID NO 14

HBE-F-Std43: 5'-AAA GTA TAG TAA GAT GTA TAG TA GCCCCAGTTGCCGTCTAGGA-3' SEQ ID NO 16

3.HBE-prim-20-Biot: 3'-TTT ZAT ATZ ATT ZTA ZAT ATZ AT-CGGGGTCAACGGCAGATCCT-Biot-5' SEQ ID NO 15

HBE-F-Std43: 5'-AAA GTA TAG TAA GAT GTA TAG TA GCCCCAGTTGCCGTCTAGGA-3' SEQ ID NO 16

MYC: 2. 3'-CAT AAA CTC ATT CAT TAA CTA ACT-AGGAGGAATACGGAGATAGTA-Biot-5' SEQ ID NO 19

MYC-F-Std45: 5'-GTA TTT GAG TAA GTA ATT GAT TGA TCCTCCTTATGCCTCTATCAT-3' SEQ ID NO 21

3.MYC-prim-21-Biot: 3'-ZAT AAA ZTZ ATT ZAT TAA ZTA AZT-AGGAGGAATACGGAGATAGTA-Biot-5' SEQ ID NO 20

MYC-F-Std45: 5'-GTA TTT GAG TAA GTA ATT GAT TGA TCCTCCTTATGCCTCTATCAT-3' SEQ ID NO 21

Procedure: The same as in other Examples, but with these modifications.

Sample preparation:

| Components | GAP-2 Std-Biot/Std-Temp | TOP-2 Std-Biot/Std-Temp | HBE-2 Std-Biot/Std-Temp | MYC-2 Std-Biot/Std-Temp | 2-Mix Std-Biot/Std-Temp | 3-Mix dZ-Biot/Std-Temp | $H_2O$ Negative |
|---|---|---|---|---|---|---|---|
| B-type beads | 50 fmol/ 50 µL | 50 fmol/ 50 µL | 50 fmol/ 50 µL | 50 fmol/ 50 µL | 50 fmol/ 50 µL | 50 fmol/ 50 µL | 0 fmol/ 50 µL |

| Components | GAP-3 dZ-Biot/Std-Temp | TOP-3 dZ-Biot/Std-Temp | HBE-3 dZ-Biot/Std-Temp | MYC-3 dZ-Biot/Std-Temp | 3-Mix dZ-Biot/Std-Temp | 2-Mix Std-Biot/Std-Temp | $H_2O$ Negative |
|---|---|---|---|---|---|---|---|
| C-type beads | 50 fmol/ 50 µL | 50 fmol/ 50 µL | 50 fmol/ 50 µL | 50 fmol/ 50 µL | 50 fmol/ 50 µL | 50 fmol/ 50 µL | 0 fmol/ 50 µL |

Notes: 1. Four type of home-made bead (each has 5000 beads) in 50 µL of 2x Tm hybridization buffer were applied for each reaction.

2. B-type bead indicates Luminex COOH bead conjugate to standard oligonucleotide; C-type bead indicates that Luminex COOH bead conjugate to dP containing oligonucleotide.

3. The concentration of each biotin-labeled oligo is 10 fmoles/µL.

4. 2-Mix indicates that the mixture of GAP-2, TOP-2, HBE-2, and MYC-2 (the concentration of each oligo is 10 fmoles/µL); 3-Mix indicates that the mixture of GAP-3, TOP-3, HBE-3, and MYC-3 (the concentration of each oligo is 10 fmoles/µL).

5. After hybridization, 50 µL of 1x Tm hybridization buffer containing 6 µg/mL of streptavidin-R-phycoerythrin was added to each reaction, and give 150 µL of final sample containing 2 µg/mL of streptavidin-R-phycoerythrin which was ready to be analyzed on Luminex machine.

Results. B-type beads mixture (3+10+14+19):

| Sample | Bead3 (GAP) | Bead10 (TOP) | Bead14 (HBE) | Bead19 (MYC) |
|---|---|---|---|---|
| B-MIX-GAP-2 | 6388 | 80 | 106 | 54 |
| B-MIX-TOP-2 | 92.5 | 938 | 90 | 66.5 |
| B-MIX-HBE-2 | 44 | 74 | 913.5 | 69 |
| B-MIX-MYC-2 | 74 | 51 | 84 | 1434 |
| B-MIX-2-MIX | 6283.5 | 884.5 | 1039.5 | 1457 |
| B-MIX-3-MIX | 2579 | 119 | 281 | 371 |
| B-MIX-H2O | 48 | 47 | 24 | 44 |

See FIG. 9 of U.S. Pat. No. 9,334,534, which is incorporated reference.

C-type beads mixture (3+10+14+19):

| Sample | Bead3 (GAP) | Bead10 (TOP) | Bead14 (HBE) | Bead19 (MYC) |
|---|---|---|---|---|
| C-MIX-GAP-3 | 4493.5 | 46 | 86 | 84 |
| C-MIX-TOP-3 | 69.5 | 4165 | 67 | 52 |
| C-MIX-HEB-3 | 26 | 56 | 3007 | 70 |
| C-MIX-MYC-3 | 70 | 19 | 36.5 | 3464 |
| C-MIX-3-MIX | 4418 | 4000 | 3093 | 3523 |
| C-MIX-2-MIX | 76.5 | 23 | 67.5 | 65 |
| C-MIX-H2O | 50 | 46.5 | 20 | 64 |

See FIG. 10 of U.S. Pat. No. 9,334,534, which is incorporated reference.

Example 3

Purpose: Luminex detection of the dZ containing oligo generated by primer extension.

Results: 1. The hybridization experiments demonstrate that the dP-containing oligonucleotides were successfully conjugated on to the Luminex carboxylated beads.

2. The Luminex beads with dP-containing oligo effectively distinguish between dZ-containing oligonucleotide from the standard oligonucleotide.

Oligonucleotides used in this study:

Positive control: xTAG COOH Bead3(GAP-A), Bead10 (TOP-A), Bead14(HBE-A), Bead19(MYC-A).

Coupling standard oligo to MicroPlex COOH Beads:
GAP-F-Lu3-NH2: 5'-$NH_2$-$C_{12}$-GAT TGT AAG ATT TGA TAA AGT GTA -3' (GAP-B) SEQ ID NO 24

Top-F-Lu10-NH2: 5'-$NH_2$-$C_{12}$-TGT AGA TTT GTA TGT ATG TAT GAT -3' (TOP-B) SEQ ID NO 25

HBE-F-Lu14-NH2: 5'-$NH_2$-$C_{12}$-AAA GTA TAG TAA GAT GTA TAG TAG -3' (HBE-B) SEQ ID NO 26

MYC-F-Lu19-NH2: 5'-$NH_2$-$C_{12}$-GTA TTT GAG TAA GTA ATT GAT TGA -3' (MYC-B) SEQ ID NO 27

Coupling dP containing oligo to MicroPlex COOH Beads:
GAP-F-Lu3-NH2-5P: 5'- $NH_2$-$C_{12}$-GAT TPT AAP ATT TPA TAA APT PTA -3' (GAP-C) SEQ ID NO 28

Top-F-Lu10-NH2-5P: 5'-$NH_2$-$C_{12}$-TGT APA TTT PTA TPT ATP TAT PAT -3' (TOP-C) SEQ ID NO 29

HBE-F-Lu14-NH2-5P: 5'-$NH_2$-$C_{12}$-AAA PTA TAP TAA PAT PTA TAP TAG -3' (HBE-C) SEQ ID NO30

MYC-F-Lu19-NH2-5P: 5'-$NH_2$-$C_{12}$-GTA TTT PAP TAA PTA ATT PAT TPA -3' (MYC-C) SEQ ID NO 31

Complementary biotin labeled oligonucleotides:
GAP: 1.Lua3-Std24-Biot: 3'-CTA ACA TTC TAA ACT ATT TCA CAT-Biot-5' SEQ ID NO 1

2. 3'-CTA ACA TTC TAA ACT ATT TCA CAT-GGACTGGACGGCAGATCTTTT-Biot-5' SEQ ID NO 2

GAP-F-Std45: 5'-GAT TGT AAG ATT TGA TAA AGT GTA CCTGACCTGCCGTCTAGAAAA-3' SEQ ID NO 4

3.GAP-prim-21-Biot: 3'-ZTA AZA TTZ TAA AZT ATT TZA ZAT-GGACTGGACGGCAGATCTTTT-Biot-5' SEQ ID NO 3

GAP-F-Std45: 5'-GAT TGT AAG ATT TGA TAA AGT GTA CCTGACCTGCCGTCTAGAAAA-3' SEQ ID NO4

4.GAP-prim-21-Biot: 3'-CTA AZA TTZ TAA AZT ATT TZA ZAT-GGACTGGACGGCAGATCTTTT-Biot-5' SEQ ID NO 5

GAP-F-45-5P: 5'-GAT TPT AAP ATT TPA TAA APT PTA CCTGACCTGCCGTCTAGAAAA-3' SEQ ID NO 6

TOP: 1.Lua10-Std24-Biot: 3'-ACA TCT AAA CAT ACA TAC ATA CTA-Biot-5' SEQ ID NO 7

2. 3'-ACA TCT AAA CAT ACA TAC ATA CTA-CTGTCGGGGCCTACTCTTG-Bio-5' SEQ ID NO 8

Top-F-Std43: 5'-TGT AGA TTT GTA TGT ATG TAT GAT GACAGCCCCGGATGAGAAC-3' SEQ ID NO 10

3.TOP-prim-19-Biot: 3'-AZA TZT AAA ZAT AZA TAZ ATA ZTA-CTGTCGGGGCCTACTCTTG-Biot-5' SEQ ID NO 9

Top-F-Std43: 5'-TGT AGA TTT GTA TGT ATG TAT GAT GACAGCCCCGGATGAGAAC-3' SEQ ID NO 10

4.TOP-prim-19-Biot: 3'-ACA TZT AAA ZAT AZA TAZ ATA ZTA-CTGTCGGGGCCTACTCTTG-Biot-5' SEQ ID NO 11

Top-F-43-5P: 5'-TGT APA TTT PTA TPT ATP TAT PAT GACAGCCCCGGATGAGAAC-3' SEQ ID NO 12

HBE: 1.Lua14-Std24-Biot: 3'-TTT CAT ATC ATT CTA CAT ATC ATC-Biot-5' SEQ ID NO13

2. 3'-TTT CAT ATC ATT CTA CAT ATC ATC-CGGGGT-CAACGGCAGATCCT-Biot-5' SEQ ID NO 14

HBE-F-Std43: 5'-AAA GTA TAG TAA GAT GTA TAG TA GCCCCAGTTGCCGTCTAGGA-3' SEQ ID NO 16

3.HBE-prim-20-Biot: 3'-TTT ZAT ATZ ATT ZTA ZAT ATZ AT-CGGGGTCAACGGCAGATCCT-Biot-5' SEQ ID NO 15

HBE-F-Std43: 5'-AAA GTA TAG TAA GAT GTA TAG TA GCCCCAGTTGCCGTCTAGGA-3' SEQ ID NO 16

4.HBE-prim-20-Biot: 3'-TTT ZAT ATZ ATT ZTA ZAT ATZ AT-CGGGGTCAACGGCAGATCCT-Biot-5' SEQ ID NO 15

HBE-F-43-5P: 5'-AAA PTA TAP TAA PAT PTA TAP TA GCCCCAGTTGCCGTCTAGGA -3' SEQ ID NO 17

MYC: 1.Lua19-Std24-Biot: 3'-CAT AAA CTC ATT CAT TAA CTA ACT-Biot-5' SEQ ID NO 18

2. 3'-CAT AAA CTC ATT CAT TAA CTA ACT-AGGAG-GAATACGGAGATAGTA-Biot-5' SEQ ID NO 19

MYC-F-Std45: 5'-GTA TTT GAG TAA GTA ATT GAT TGA TCCTCCTTATGCCTCTATCAT-3' SEQ ID NO 21

3.MYC-prim-21-Biot: 3'-ZAT AAA ZTZ ATT ZAT TAA ZTA AZT-AGGAGGAATACGGAGATAGTA-Biot-5' SEQ ID NO 20

MYC-F-Std45: 5'-GTA TTT GAG TAA GTA ATT GAT TGA TCCTCCTTATGCCTCTATCAT-3' SEQ ID NO 21

4.MYC-prim-21-Biot: 3'-CAT AAA ZTZ ATT ZAT TAA ZTA AZT-AGGAGGAATACGGAGATAGTA-Biot-5' SEQ ID NO 22

MYC-F-45-5P: 5'-GTA TTT PAP TAA PTA ATT PAT TPA TCCTCCTTATGCCTCTATCAT -3' SEQ ID NO 23

Procedure: Microspheres were protected from prolonged exposure to light throughout this procedure.

1. Select the appropriate microsphere sets (A, B, and C) and resuspend by vortex and sonicated for approximately 20 seconds.
2. Combine 5000 microspheres of each set per reaction.
3. Concentrate the microsphere mixture by centrifugation at ≥8000 x g for 1-2 minutes.
4. Remove the supernatant and resuspend to 100 of each microsphere set per µL in 2X Tm Hybridization Buffer by vortex and sonication for approximately 20 seconds. (Note: 50 µL are required for each reaction.)
5. Aliquot 50 µL of the microsphere mixture to each well.
6. Add 50 µL of H$_2$O to each background well.
7. Add 5 µL of biotinylated oligo (10 fmol/µL, complement to the oligo on the microsphere beads) to each sample wells.
8. Adjust the total volume to 100 µL by adding the appropriate volume of dH$_2$O to each sample well.
9. Cover the plate to prevent evaporation and denature at 95° C. for 120 seconds, then cool to 37° C. at a speed of 0.1° C./second (about 10 minutes).
10. Hybridize at 37° C. for another 10 minutes and then cool to room temperature.
11. Add 50 µL 1X Tm Hybridization Buffer containing streptavidin-R-phycoerythrin to give 150 µL of solution with 2 µg/mL of streptavidin-R-phycoerythrin (original concentration 2 µg/µL).
16. Incubate at 37° C. for 15 minutes, then store samples at 4° C. overnight.
17. The next day, the samples were warmed to room temperature and analyzed 45 µL at 25° C. on the Luminex analyzer according to the system manual.

Sample preparation:

| Components | GAP-B | GAP-C | TOP-B | TOP-C | HBE-B | HBE-C | MYC-B | MYC-C |
| --- | --- | --- | --- | --- | --- | --- | --- | --- |
| 1. Std24-Biot | 50 fmol/ 50 µL | 50 fmol/ 50 µL | 50 fmol/ 50 µL | 50 fmol/ 50 µL | 50 fmol/ 50 µL | 50 fmol/ 50 µL | 50 fmol/ 50 µL | 50 fmol/ 50 µL |
| 2. Std-Biot/Std-Temp | 50 fmol/ 50 µL | 50 fmol/ 50 µL | 50 fmol/ 50 µL | 50 fmol/ 50 µL | 50 fmol/ 50 µL | 50 fmol/ 50 µL | 50 fmol/ 50 µL | 50 fmol/ 50 µL |
| 3. dZ-Biot/Std-Temp | 50 fmol/ 50 µL | 50 fmol/ 50 µL | 50 fmol/ 50 µL | 50 fmol/ 50 µL | 50 fmol/ 50 µL | 50 fmol/ 50 µL | 50 fmol/ 50 µL | 50 fmol/ 50 µL |

-continued

| Components | GAP-B | GAP-C | TOP-B | TOP-C | HBE-B | HBE-C | MYC-B | MYC-C |
|---|---|---|---|---|---|---|---|---|
| 4. dZ-Biot/dP-Temp | 50 fmol/ 50 µL | 50 fmol/ 50 µL | 50 fmol/ 50 µL | 50 fmol/ 50 µL | 50 fmol/ 50 µL | 50 fmol/ 50 µL | 50 fmol/ 50 µL | 50 fmol/ 50 µL |
| $H_2O$ | 50 µL | 50 µL | 50 µL | 50 µL | 50 µL | 50 µL | 50 µL | 50 µL |

Notes:
1. 5000 beads in 50 µL of 2× Tm hybridization buffer were applied for each reaction.
2. B-type bead indicates Luminex COOH bead conjugate to standard oligonucleotide; C-type bead indicates that Luminex COOH bead conjugate to dP containing oligonucleotide.
3. A-type bead was bought from Luminex with standard oligo conjugated, which is positive control for B-type bead.
4. The concentration of each biotin-labeled oligo is 10 fmoles/µL.
5. After hybridization, 50 µL of 1× Tm hybridization buffer containing 6 µg/mL of streptavidin-R-phycoerythrin was added to each reaction, and give 150 µL of final sample containing 2 µg/mL of streptavidin-R-phycoerythrin which was ready to be analyzed on Luminex machine.
Results: See also FIGS. 10 and 11 of U.S. Pat. No. 9,334,534, which is incorporated reference.

GAP:

| Components | GAP-A | GAP-B | GAP-C |
|---|---|---|---|
| 1. Std24-Biot | 13246.5 | 15551 | 182 |
| 2. Std-Biot/Std-Temp | | 5844 | 13.5 |
| 3. dZ-Biot/Std-Temp | | 3080 | 4916 |
| 4. dZ-Biot/dP-Temp | | 2051 | 3194 |
| $H_2O$ | | 71.5 | 64.5 |

TOP:

| Components | TOP-A | TOP-B | TOP-C |
|---|---|---|---|
| 1. Std24-Biot | 16806 | 7057.5 | 182.5 |
| 2. Std-Biot/Std-Temp | | 1355.5 | 80 |
| 3. dZ-Biot/Std-Temp | | 82 | 4520.5 |
| 4. dZ-Biot/dP-Temp | | 173.5 | 2643.5 |
| $H_2O$ | | 102 | 19 |

HBE:

| Components | HBE-A | HBE-B | HBE-C |
|---|---|---|---|
| 1. Std24-Biot | 19951 | 6921 | 18 |
| 2. Std-Biot/Std-Temp | | 1713 | 120 |
| 3. dZ-Biot/Std-Temp | | 562.5 | 3392 |
| 4. dZ-Biot/dP-Temp | | 526 | 3058 |
| $H_2O$ | | 33.5 | 57 |

MYC:

| Components | MYC-A | MYC-B | MYC-C |
|---|---|---|---|
| 1. Std24-Biot | 14389.5 | 6047.5 | 283.5 |
| 2. Std-Biot/Std-Temp | | 1874 | 85 |
| 3. dZ-Biot/Std-Temp | | 636 | 4254.5 |
| 4. dZ-Biot/dP-Temp | | 337.5 | 2676 |
| $H_2O$ | | 88.5 | 130 |

Example 4

Purpose: To compare the efficiency and fidelity of DNA polymerases (Taq, Vent (exo+), and DV (exo+)) to incorporate dZTP opposite two consecutive dPs in the template.

ThermoPol Reaction Buffer (20 mM Tris-HCl, 10 mM $(NH_4)_2SO_4$, 10 mM KCl, 2 mM $MgSO_4$, 0.1% Triton X-100, pH=8.0).

Results: 1. The order of the Fidelity of the polymerases tested is Deep Vent (exo+)>Vent (exo+)>Taq.
2. In the absence of dZTP, Deep Vent and Vent just mis-incorporate one dCTP opposite the first dP. However, Taq can mis-incorporate dCTP opposite two consecutive dPs, then keep extending primer.
3. The extension efficiency of Vent (exo+) seems better than DV (exo+) and Taq, this observation need to be tested using real-time PCR.

Oligonucletotides used in this study:
Negative control (−): dNTP (each 0.1 mM)
$T_m=59$  T7-Y-RS-S16:  3'-GAAATCACTCCCAAT-TAAGCG-5' SEQ ID NO 32
T7-PP-Temp:  5'-GCGTAATACGACTCACTATA-GACGAPPCTACTTTAGTGAGGGTTAATTCGC-3' SEQ ID NO 33

Positive control (+): dNTP (each 0.1 mM), and dZTP (0.1 mM)
$T_m=59$  T7-Y-RS-S16:  3'-GAAATCACTCCCAAT-TAAGCG-5' SEQ ID NO 32
T7-PP-Temp:  5'-GCGTAATACGACTCACTATA-GACGAPPCTACTTTAGTGAGGGTTAATTCGC-3' SEQ ID NO 33

Procedure: 5'-$^{32}$P-labeled primer T7-Y-RS-S16 (0.2 pmole of hot primer plus 4 pmole of cold prime, final assay concentration 70 nM) was annealed to template T7-PP-Temp (6 pmole, final assay concentration 100 nM) in 1× Thermopol polymerase reaction buffer (pH=8.0 at room temperature) by heating (5 min at 95° C.) and then slow cooling (0.5 h) to room temperature. dNTP (each final 0.1 mM), and dZTP (final 0.1 mM, with (+) or without (−)) were added at room temperature. The reaction mixture was cooled to 4° C. for 1 min and followed by the addition of Taq (2.5 units), Vent (exo+), or Deep Vent (exo+) DNA polymerase (2 units for Vent and DV) to give a final volume of 60 µL. The primer was extended at 65° C. and aliquots (7) were taken from each reaction at time intervals (1, 2, 4, 8, and 16 min), quenched by PAGE loading/quench buffer (7 µL, 10 mM EDTA in formamide). Samples were resolved by electrophoresis using a 16% PAGE (7 M urea). The gel was analyzed using MolecularImager software. See FIG. 12 of U.S. Pat. No. 9,334,534, which is incorporated reference.

Example 5

Purpose: Compare the PCR efficiency of different template containing one dP, two dPs under the conditions of with dZ/PTPs or without dZ/PTPs.

Summary of the results (see also FIG. 13 of U.S. Pat. No. 9,334,534, which is incorporated reference.): 1. At pH=8.0, the PCR efficiency of dNTPs is better than that of dNTPs+dZ/PTPs;

2. In the absence of dZ/PTPs, there is significant amount of product generated from the dP containing template after 26 cycles of PCR amplification.
3. Using real-time PCR to monitor the PCR process.

Oligonucleotides used in his study:

T7-Z-RS-S16:   5'-GCGTAATACGACTCACTATAG-3' Tm=57.2 SEQ ID NO 34

T7-G-51-Std:   5'-GCGTAATACGACTCACTATA-GACGAGCGTACTTTAGTGAGGGTTAATTCGC-3' SEQ ID NO 35

T7-P-Temp:   5'-GCGTAATACGACTCACTATA-GACGAPCGTACTTTAGTGAGGGTTAATTCGC-5' SEQ ID NO 36

T7-PP-Temp:   5'-GCGTAATACGACTCACTATA-GACGAPPCTACTTTAGTGAGGGTTAATTCGC-3' SEQ ID NO 33

Tm=59   T7-Y-RS-S16:   3'-GAAATCACTCCCAAT-TAAGCG-5' SEQ ID NO 32

Procedure:

| Components | Volume (µl) | Final Concentration |
|---|---|---|
| Nuclease-Free Water (final volume of 40 µl) | 17 | |
| Forward Primer: T7-Z-RS-S16 (10 pmol/µl) | 1 | 0.25 µM |
| Reverse Primer: T7-Y-RS-S16 (10 pmol/µl) | 1 | 0.25 µM |
| Template: Three different Templates (A, B, and C) (0.01 pmol/µl) | 1 + 4 (H2O) | 0.25 nM |
| 10× Thermopol Buffer (pH = 8.0) | 4 | |
| dNTP (2 mM) | 4 | 0.2 mM each |
| dZTP (2 mM) | 4 | 0.2 mM |
| dPTP (2 mM) | 4 | 0.2 mM |
| Hot Start Taq (5 U/µl) | 0.5 | 0.06 U/µl |

Note:
1× ThermoPol Reaction Buffer (20 mM Tris-HCl, 10 mM (NH4)2SO4, 10 mM KCl, 2 mM MgSO4, 0.1% Tritonx-100, pH 8.0 at at 25° C.).
PCR conditions: one cycle of 95° C. for 15 min; 26 cycles of 95° C. for 20 s, (55° C. for 30 s, 72° C. for 1 min or 2 min; 72° C. for 5 min; 4° C. forever.

Results:
T7-G-51-Std:   5'-GCGTAATACGACTCACTATA-GACGAGCGTACTTTAGTGAGGGTTAATTCGC-3' SEQ ID NO 35
(Template-A)
T7-P-Temp:   5'-GCGTAATACGACTCACTATA-GACGAPCGTACTTTAGTGAGGGTTAATTCGC-5' SEQ ID NO 36
(Template-B)
T7-PP-Temp:   5'-GCGTAATACGACTCACTATA-GACGAPPCTACTTTAGTGAGGGTTAATTCGC-3' SEQ ID NO 33
(Template-C)
3'-GTCGTTAAGACTTGTTCGGAGAGTA-5' Tm=65° C. SEQ ID NO 37
5'-CCGCAGTACAACCCAGGGGACAAAGATAC-CAAAATTGCCAAGAGGATGGCTGTGTT GATCTT-CACCGACTTCATATGCATGGCCCCAATCTCATTC-TATGCTCTGTCAGCAATT CTGAACAAGCCTCCAT-3' SEQ ID NO 38
3'-GGCGTCATGTTGGGTCCCCTGTTTCTATGGTTT-TAACGGTTCTCCTACCGACACAACT AGAAGTGGCTGAAGTATACGTACCGGGGT-TAGAGTAAGATACGAGACAGTCGTTAA GACTTGTTCGGAGGTA-5' SEQ ID NO 39

Literature

| | |
|---|---|
| [Bro97] | Brownie, J., Shawcross, S., Theaker, J., Whitcombe, D., Ferrie, R., Newton, C., Little, S. (1997). The elimination of primer-dimer accumulation in PCR. *Nucleic Acids Res.* 25, 3235-3241 |
| [Elb04a] | Elbeik, T., Markowitz, N., Nassos, P., Kumar, U., Beringer, S., Haller, B. and Ng, V. (2004) Simultaneous runs of the Bayer VERSANT HIV-1 version 3.0 and HCV bDNA version 3.0 quantitative assays on the system 340 platform provide reliable quantitation and improved work flow. *J. Clin. Microbiol.*, 42, 3120-3127. |
| [Elb04b] | Elbeik, T., Surtihadi, J., Destree, M., Gorlin, J., Holodniy, M., Jortani, S.A., Kuramoto, K., Ng, V., Valdes, R., Valsamakis, A. et al. (2004) Multicenter evaluation of the performance characteristics of the Bayer VERSANT HCV RNA 3.0 assay (bDNA). *J. Clin. Microbiol.*, 42, 563-569. |
| [Hor95] | Horlacher, J., Hottiger, M., Podust, V.N., Hübscher, U., Benner, S.A. (1995) Recognition by viral and cellular DNA polymerases of nucleosides bearing bases with non-standard hydrogen bonding patterns. *Proc. Natl. Acad. Sci.*, 92, 6329-6333 |
| [Hut03] | Hutter, D. and Benner, S.A. (2003) Expanding the genetic alphabet. Non-epimerizing nucleoside with the pyDDA hydrogen bonding pattern. *J. Org. Chem.*, 68, 9839-9842 |
| [Joh04] | Johnson, S.C., Sherrill, C.B., Marshall, D.J., Moser, M.J., Prudent, J.R. (2004) A third base pair for the polymerase chain reaction: inserting isoC and isoG. *Nucleic Acids Res.* 32, 1937-1941 |
| [Jur00] | Jurczyk, S.C., Horlacher, J., Devine, K.G., Benner, S.A., Battersby, T.R. (2000) Synthesis and characterization of oligonucleotides containing 2'-deoxyxanthosine using phosphoramidite chemistry. *Helv. Chim. Acta* 83, 1517-1524 |
| [Jur98] | Jurczyk, S., Kodra, J.T., Rozzell, J.D., Jr., Benner, S.A., Battersby, T.R. (1998) Synthesis of oligonucleotides containing 2'-deoxyisoguanosine and 2'-deoxy-5-methyliso-cytidine using phosphoramidite chemistry. *Helv. Chim. Acta* 81, 793-811] |
| [Jur99] | Jurczyk, S.C., Battersby, T.R., Kodra, J.T., Park, J.-H., Benner, S.A. (1999) Synthesis of 2'-deoxyisoguanosine triphosphate and 2'-deoxy-5-methyl-isocytidine triphosphate. *Helv. Chim. Acta*. 82, 1005-1015 |
| [Kim09] | Kim, H.J., Leal, N.A., Benner, S.A. (2009) 2'-Deoxy-1-methylpseudocytidine, a stable analog of 2'-deoxy-5-methylisocytidine. *Bioorg Med. Chem.* 17, 3728-373 |
| [Kod97] | Kodra, J., Benner, S.A. (1997) Synthesis of an N-alkyl derivative of 2'-deoxyisoguanosine. *Syn. Lett.*, 939-940 |
| [Lut99] | Lutz, S., Burgstaller, P., Benner, S.A. (1999) An in vitro screening technique for polymerases that can incorporate modified nucleotides. Pseudouridine as a substrate for thermostable polymerases. *Nucl. Acids Res.* 27, 2792-2798] |

| [Mar04] | Martinot, T.A., Benner, S.A. (2004) Expanding the genetic alphabet: 7-Deaza-isoguanosine favors the 1N—H keto form by $10^3$-to-1 over the enol. *J. Org. Chem.* 69, 3972-3975 |
|---|---|
| [Mur91] | Murakami, K., Shirasaka, T., Yoshioka, H., Kojima, E., Aoki, S., Ford, Jr., H., Driscoll, J.S., Kelley, J.A., Mitsuya, H. (1991) *Escherichia coli* mediated biosynthesis and in vitro Anti-HIV Activity of lipophilic 6-Halo-2',3'-dideoxypurine nucleosides. *J. Med. Chem.* 34, 1606-1612 |
| [Pic90] | Piccirilli, J.A., Krauch, T., Moroney, S.E., Benner, S.A. (1990) Extending the genetic alphabet. Enzymatic incorporation of a new base pair into DNA and RNA. *Nature* 343, 33-37 |
| [Pic91] | Piccirilli, J.A., Krauch, T., MacPherson, L.J., Benner, S.A. (1991) A direct route to 3-(ribofuranosyl)-pyridine nucleosides. *Helv. Chim. Acta* 74, 397-406 |
| [Sep76] | Sepiol, J., Kazimierczuk, Z., Shugar, D.Z. (1976) Tautomerism of iso-guanosine and solvent-induced keto-enol equilibrium. *Z. Naturforsch* 31C, 361-370 |
| [Sis05] | Sismour, A.M., Benner, S.A. (2005) The use of thymidine analogs to improve the replication of an extra DNA base pair: A synthetic biological system. *Nucl. Acids Res.* 33, 5640-5646 |
| [Swi89] | Switzer, C.Y., Moroney, S.E., Benner, S.A. (1989) Enzymatic incorporation of a new base pair into DNA and RNA. *J. Am. Chem. Soc.* 111, 8322-8323 |
| [Swi93] | Switzer, C.Y., Moroney, S.E., Benner, S.A. (1993) Enzymatic recognition of the base pair between iso-cytidine and iso-guanosine. *Biochemistry* 32, 10489-10496 |
| [Tan06] | Tang, Y., Ramaiah, M., Vince, R. (2006) Synthesis and biological evaluation of carboacyclic nucleosides with (Z) and (E)-9-[4,4-bis(hydroxymethyl)]-2-butenyl side chain. *Bioorg. Med. Chem. Lett.* 14, 5866-5875 |
| [Voe93] | Voegel, J.J., von Krosigk, U., Benner, S.A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547 |
| [Voe96a] | Voegel, J.J., Benner, S.A. (1996) Synthesis and characterization of non-standard nucleosides and nucleotides bearing the acceptor-donor-donor pyrimidine analog 6-amino-3-methylpyrazin-2-one. *Helv. Chim. Acta* 79, 1863-1880 |
| [Voe96b] | Voegel, J.J., Benner, S.A. (1996) Synthesis, molecular recognition & enzymology of oligonucleotides containing the non-standard base pair between 5-aza-7-deaza-iso-guanine & 6-amino-3-methylpyrazin-2-one, a donor-acceptor-acceptor purine analog and an acceptor-donor-donor pyrimidine analog. *Helv. Chim. Acta* 79, 1881-1898 |
| [Von95] | von Krosigk, U., Benner, S.A. (1995) pH-independent triple helix formation by an oligonucleotide containing a pyrazine donor-donor-acceptor base. *J. Am. Chem. Soc.* 117, 5361-5362 |
| [Yan06] | Yang, Z., Hutter, D., Sheng, P., Sismour, A.M. and Benner, S.A. (2006) Artificially expanded genetic information system. A new base pair with an alternative hydrogen bonding pattern. *Nucleic Acids Res.*, 34, 6095-6101. |
| [Yan07] | Yang, Z., Sismour, A.M., Sheng, P., Puskar, N.L., Benner, S.A. (2007) Enzymatic incorporation of a third nucleobase pair. *Nucl. Acids Res.* 35, 4238-4249 |

What is claimed is:

1. A process for constructing a DNA duplex comprising only standard nucleotides, said process comprising:

(a) synthesizing a plurality of single stranded oligonucleotide fragments that are designed to hybridize to form a hybridized concatamer, wherein said fragments comprise 5'-hybridizing regions, 3'-hybridizing regions and, optionally, regions between the 5'-hybridizing regions and 3'-hybridizing regions, wherein said oligonucleotide fragments contain one or more non-standard nucleobases having nucleobase analogs selected from the group consisting of methyl-pseudocytosine, methyl-isocytosine, 7-deaza-isoguanine, isoguanine, amino-nitropyridone, and 2-amino-imidazo-[1,2a]-1, 5-triazin-[8H]-4-one, (b) contacting said fragments in an aqueous solution where they form a hybridized concatamer, wherein said hybridized concatamer is held together by the pairing of adenine with thymine, guanine[,] with cytosine, amino-nitropyridone with 2-amino-imidazo-[1,2a]-1,3, 5-triazin-[8H]-4-one, and methyl-pseudocytosine or methyl-isocytosine paired with 7-deaza-isoguanine or isoguanine, and then (c) filling in gaps in said concatamer by incubating the concatamer with nucleoside triphosphates and a DNA polymerase that is unable to displace strands under conditions where it fills said gaps, and then (d) ligating said fragments to give a covalently joined concatamer, and (e) PCR amplifying said covalently joined concatamer under conditions where any amino-nitropyridone present in a template directs the incorporation of guanine opposite to it, and any 7-deaza-isoguanine or isoguanine present in a template directs incorporation of thymine opposite it.

2. The process of claim 1 wherein the nucleobase analogs in said non-standard nucleobases are selected from the group consisting of amino-nitropyridone and 2-amino-imidazo-[1,2a]-1,3,5-triazin-[8H]-4-one.

3. The process of claim 1 wherein the nucleobase analogs in said non-standard nucleobases are selected from the group consisting of methyl-pseudocytosine, methyl-isocytosine, 7-deaza-isoguanine, and isoguanine.

\* \* \* \* \*

SEQUENCE LISTING

<160> NUMBER OF SEQ ID NOS: 39

<210> SEQ ID NO 1
<211> LENGTH: 24
<212> TYPE: DNA
<213> ORGANISM: Artificial Sequence
<220> FEATURE:
<223> OTHER INFORMATION: synthetic

<400> SEQUENCE: 1
tacactttat caaatcttac aatc                                          24

<210> SEQ ID NO 2
<211> LENGTH: 45
<212> TYPE: DNA
<213> ORGANISM: Artificial Sequence
<220> FEATURE:
<223> OTHER INFORMATION: synthetic

<400> SEQUENCE: 2
ttttctagac ggcaggtcag gtacacttta tcaaatctta caatc                   45

<210> SEQ ID NO 3
<211> LENGTH: 45
<212> TYPE: DNA
<213> ORGANISM: Artificial Sequence

```
<220> FEATURE:
<223> OTHER INFORMATION: synthetic
<220> FEATURE:
<221> NAME/KEY: misc_feature
<222> LOCATION: (24)..(24)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (32)..(32)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (41)..(41)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (45)..(45)
<223> OTHER INFORMATION: 6-amino-3-(2'-deoxy)-D-ribofuranosyl)-5-nitro-
      1H-pyridin-2-one

<400> SEQUENCE: 3
ttttctagac ggcaggtcag gtananttta tnaaatntta naatn              45

<210> SEQ ID NO 4
<211> LENGTH: 45
<212> TYPE: DNA
<213> ORGANISM: Artificial Sequence
<220> FEATURE:
<223> OTHER INFORMATION: synthetic

<400> SEQUENCE: 4
gattgtaaga tttgataaag tgtacctgac ctgccgtcta gaaaa              45

<210> SEQ ID NO 5
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (24)..(24)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (32)..(32)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (41)..(41)
```

<223> OTHER INFORMATION: 6-amino-3-(2'-deoxy)-D-ribofuranosyl)-5-nitro-
      1H-pyridin-2-one

<400> SEQUENCE: 5 tttctagac ggcaggtcag gtananttta tnaaatntta naatc                45

<210> SEQ ID NO 6
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (9)..(9)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (14)..(14)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (20)..(20)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (22)..(22)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 6
gattntaana tttnataaan tntacctgac ctgccgtcta gaaaa             45

<210> SEQ ID NO 7
<211> LENGTH: 24
<212> TYPE: DNA
<213> ORGANISM: Artificial Sequence
<220> FEATURE:
<223> OTHER INFORMATION: synthetic

<400> SEQUENCE: 7
atcatacata catacaaatc taca                                    24

<210> SEQ ID NO 8
<211> LENGTH: 43
<212> TYPE: DNA
<213> ORGANISM: Artificial Sequence
<220> FEATURE:
<223> OTHER INFORMATION: synthetic

<400> SEQUENCE: 8
gttctcatcc ggggctgtca tcatacatac atacaaatct aca               43

<210> SEQ ID NO 9
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (22)..(22)
<223> OTHER INFORMATION: 6-amino-3-(2'-deoxy)-D-ribofuranosyl)-5-nitro-

```
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (30)..(30)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (34)..(34)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (42)..(42)
<223> OTHER INFORMATION: 6-amino-3-(2'-deoxy)-D-ribofuranosyl)-5-nitro-
      1H-pyridin-2-one

<400> SEQUENCE: 9
gttctcatcc ggggctgtca tnatanatan atanaaatnt ana                    43

<210> SEQ ID NO 10
<211> LENGTH: 43
<212> TYPE: DNA
<213> ORGANISM: Artificial Sequence
<220> FEATURE:
<223> OTHER INFORMATION: synthetic

<400> SEQUENCE: 10
tgtagatttg tatgtatgta tgatgacagc cccggatgag aac                    43

<210> SEQ ID NO 11
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (22)..(22)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (30)..(30)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (34)..(34)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one

<400> SEQUENCE: 11
gttctcatcc ggggctgtca tnatanatan atanaaatnt aca                    43
```

<210> SEQ ID NO 12
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (10)..(10)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (14)..(14)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (18)..(18)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (22)..(22)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 12
tgtanatttn tatntatnta tnatgacagc cccggatgag aac           43

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
ctactataca tcttactata cttt                                24

<210> SEQ ID NO 14
<211> LENGTH: 44
<212> TYPE: DNA
<213> ORGANISM: Artificial Sequence
<220> FEATURE:
<223> OTHER INFORMATION: synthetic

<400> SEQUENCE: 14
tcctagacgg caactggggc ctactataca tcttactata cttt          44

<210> SEQ ID NO 15
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (28)..(28)
<223> OTHER INFORMATION: 6-amino-3-(2'-deoxy)-D-ribofuranosyl)-5-nitro-
      1H-pyridin-2-one

```
<220> FEATURE:
<221> NAME/KEY: misc_feature
<222> LOCATION: (31)..(31)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (35)..(35)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (40)..(40)
<223> OTHER INFORMATION: 6-amino-3-(2'-deoxy)-D-ribofuranosyl)-5-nitro-
      1H-pyridin-2-one

<400> SEQUENCE: 15
tcctagacgg caactggggc tantatanat nttantatan ttt                    43

<210> SEQ ID NO 16
<211> LENGTH: 43
<212> TYPE: DNA
<213> ORGANISM: Artificial Sequence
<220> FEATURE:
<223> OTHER INFORMATION: synthetic

<400> SEQUENCE: 16
aaagtatagt aagatgtata gtagccccag ttgccgtcta gga                    43

<210> SEQ ID NO 17
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (9)..(9)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (13)..(13)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (16)..(16)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (21)..(21)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 17
aaantatant aanatntata ntagccccag ttgccgtcta gga                    43

<210> SEQ ID NO 18
<211> LENGTH: 24
<212> TYPE: DNA
<213> ORGANISM: Artificial Sequence
<220> FEATURE:
<223> OTHER INFORMATION: synthetic

<400> SEQUENCE: 18
```
tcaatcaatt acttactcaa atac                                          24

<210> SEQ ID NO 19
<211> LENGTH: 45
<212> TYPE: DNA
<213> ORGANISM: Artificial Sequence
<220> FEATURE:
<223> OTHER INFORMATION: synthetic

<400> SEQUENCE: 19
atgatagagg cataaggagg atcaatcaat tacttactca aatac                   45

<210> SEQ ID NO 20
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (27)..(27)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (33)..(33)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (45)..(45)
<223> OTHER INFORMATION: 6-amino-3-(2'-deoxy)-D-ribofuranosyl)-5-nitro-
      1H-pyridin-2-one

<400> SEQUENCE: 20
atgatagagg cataaggagg atnaatnaat tanttantna aatan                   45

<210> SEQ ID NO 21
<211> LENGTH: 45
<212> TYPE: DNA
<213> ORGANISM: Artificial Sequence
<220> FEATURE:
<223> OTHER INFORMATION: synthetic

<400> SEQUENCE: 21
gtatttgagt aagtaattga ttgatcctcc ttatgcctct atcat                   45

<210> SEQ ID NO 22
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-amino-3-(2'-deoxy)-D-ribofuranosyl)-5-nitro-

```
    1H-pyridin-2-one
<220> FEATURE:
<221> NAME/KEY: misc_feature
<222> LOCATION: (27)..(27)
<223> OTHER INFORMATION: 6-amino-3-(2'-deoxy)-D-ribofuranosyl)-5-nitro-
    1H-pyridin-2-one
<220> FEATURE:
<221> NAME/KEY: misc_feature
<222> LOCATION: (33)..(33)
<223> OTHER INFORMATION: 6-amino-3-(2'-deoxy)-D-ribofuranosyl)-5-nitro-
    1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
    1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
    1H-pyridin-2-one

<400> SEQUENCE: 22
atgatagagg cataaggagg atnaatnaat tanttantna aatac              45

<210> SEQ ID NO 23
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 2-amino-8-(beta-D-2'-deoxyribofuranosyl)-
    imidazo-[1,2a]-1,3,5-triazin-[8H]-4-one
<220> FEATURE:
<221> NAME/KEY: misc_feature
<222> LOCATION: (9)..(9)
<223> OTHER INFORMATION: 2-amino-8-(beta-D-2'-deoxyribofuranosyl)-
    imidazo-[1,2a]-1,3,5-triazin-[8H]-4-one
<220> FEATURE:
<221> NAME/KEY: misc_feature
<222> LOCATION: (13)..(13)
<223> OTHER INFORMATION: 2-amino-8-(beta-D-2'-deoxyribofuranosyl)-
    imidazo-[1,2a]-1,3,5-triazin-[8H]-4-one
<220> FEATURE:
<221> NAME/KEY: misc_feature
<222> LOCATION: (19)..(19)
<223> OTHER INFORMATION: 2-amino-8-(beta-D-2'-deoxyribofuranosyl)-
    imidazo-[1,2a]-1,3,5-triazin-[8H]-4-one
<220> FEATURE:
<221> NAME/KEY: misc_feature
<222> LOCATION: (23)..(23)
<223> OTHER INFORMATION: 2-amino-8-(beta-D-2'-deoxyribofuranosyl)-
    imidazo-[1,2a]-1,3,5-triazin-[8H]-4-one

<400> SEQUENCE: 23
gtatttnant aantaattna ttnatcctcc ttatgcctct atcat              45

<210> SEQ ID NO 24
<211> LENGTH: 24
<212> TYPE: DNA
<213> ORGANISM: Artificial Sequence
<220> FEATURE:
<223> OTHER INFORMATION: synthetic

<400> SEQUENCE: 24
gattgtaaga tttgataaag tgta                                     24

<210> SEQ ID NO 25
<211> LENGTH: 24
<212> TYPE: DNA
```

```
<213> ORGANISM: Artificial Sequence
<220> FEATURE:
<223> OTHER INFORMATION: synthetic

<400> SEQUENCE: 25
tgtagatttg tatgtatgta tgat                                              24

<210> SEQ ID NO 26
<211> LENGTH: 24
<212> TYPE: DNA
<213> ORGANISM: Artificial Sequence
<220> FEATURE:
<223> OTHER INFORMATION: synthetic

<400> SEQUENCE: 26
aaagtatagt aagatgtata gtag                                              24

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
gtatttgagt aagtaattga ttga                                              24

<210> SEQ ID NO 28
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (9)..(9)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (14)..(14)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (20)..(20)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (22)..(22)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 28
gattntaana tttnataaan tnta                                              24

<210> SEQ ID NO 29
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
```

<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (10)..(10)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (14)..(14)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (18)..(18)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (22)..(22)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 29
tgtanatttn tatntatnta tnat                                              24

<210> SEQ ID NO 30
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (9)..(9)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (13)..(13)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (16)..(16)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (21)..(21)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 30
aaantatant aanatntata ntag                                              24

<210> SEQ ID NO 31
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (9)..(9)

```
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (13)..(13)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (19)..(19)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (23)..(23)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 31
gtatttnant aantaattna ttna                                            24

<210> SEQ ID NO 32
<211> LENGTH: 21
<212> TYPE: DNA
<213> ORGANISM: Artificial Sequence
<220> FEATURE:
<223> OTHER INFORMATION: synthetic

<400> SEQUENCE: 32
gcgaattaac cctcactaaa g                                               21

<210> SEQ ID NO 33
<211> LENGTH: 51
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (26)..(26)
<223> OTHER INFORMATION: 2-amino-8-(beta-D-2'-deoxyribofuranosyl)-
      imidazo-[1,2a]-1,3,5-triazin-[8H]-4-one
<220> FEATURE:
<221> NAME/KEY: misc_feature
<222> LOCATION: (27)..(27)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 33
gcgtaatacg actcactata gacganncta ctttagtgag ggttaattcg c              51

<210> SEQ ID NO 34
<211> LENGTH: 21
<212> TYPE: DNA
<213> ORGANISM: Artificial Sequence
<220> FEATURE:
<223> OTHER INFORMATION: synthetic

<400> SEQUENCE: 34
gcgtaatacg actcactata g                                               21

<210> SEQ ID NO 35
<211> LENGTH: 51
<212> TYPE: DNA
<213> ORGANISM: Artificial Sequence
<220> FEATURE:
<223> OTHER INFORMATION: synthetic

<400> SEQUENCE: 35
gcgtaatacg actcactata gacgagcgta ctttagtgag ggttaattcg c              51
```

```
<210> SEQ ID NO 36
<211> LENGTH: 51
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (26)..(26)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 36
gcgtaatacg actcactata gacgancgta ctttagtgag ggttaattcg c         51

<210> SEQ ID NO 37
<211> LENGTH: 25
<212> TYPE: DNA
<213> ORGANISM: Artificial Sequence
<220> FEATURE:
<223> OTHER INFORMATION: synthetic

<400> SEQUENCE: 37
atgagaggct tgttcagaat tgctg                                      25

<210> SEQ ID NO 38
<211> LENGTH: 130
<212> TYPE: DNA
<213> ORGANISM: Artificial Sequence
<220> FEATURE:
<223> OTHER INFORMATION: synthetic

<400> SEQUENCE: 38
ccgcagtaca acccagggga caaagatacc aaaattgcca agaggatggc tgtgttgatc   60
ttcaccgact tcatatgcat ggccccaatc tcattctatg ctctgtcagc aattctgaac  120
aagcctccat                                                        130

<210> SEQ ID NO 39
<211> LENGTH: 130
<212> TYPE: DNA
<213> ORGANISM: Artificial Sequence
<220> FEATURE:
<223> OTHER INFORMATION: synthetic

<400> SEQUENCE: 39
atggaggctt gttcagaatt gctgacagag catagaatga gattggggcc atgcatatga   60
agtcggtgaa gatcaacaca gccatcctct tggcaatttt ggtatctttg tccctgggt   120 tgtactgcgg                                                        130
```